(12) United States Patent
Zhelev et al.

(10) Patent No.: US 7,964,415 B2
(45) Date of Patent: Jun. 21, 2011

(54) STABLE WATER-SOLUBLE POLYETHYLENIMINE CONJUGATES AND METHODS OF USE THEREOF

(75) Inventors: Pavel Zhelev, Toronto (CA); Amer Alagic, Toronto (CA); Yahia A. Gawad, Mississauga (CA)

(73) Assignee: CardioGenics Inc., Mississauga, Ontario (CA)

( * ) Notice: Subject to any disclaimer, the term of this patent is extended or adjusted under 35 U.S.C. 154(b) by 689 days.

(21) Appl. No.: 11/411,552

(22) Filed: Apr. 26, 2006

(65) Prior Publication Data

US 2007/0254285 A1 Nov. 1, 2007

(51) Int. Cl.
*G01N 33/544* (2006.01)
*G01N 33/532* (2006.01)
*G01N 33/53* (2006.01)

(52) U.S. Cl. ........ 436/528; 436/544; 436/106; 436/111; 435/7.1; 435/7.5

(58) Field of Classification Search .................. None
See application file for complete search history.

(56) References Cited

U.S. PATENT DOCUMENTS

| | | | |
|---|---|---|---|
| 4,288,552 A | 9/1981 | Gestralius | |
| 4,386,158 A | 5/1983 | Shimizu et al. | |
| 4,681,843 A | 7/1987 | Egerer et al. | |
| 4,749,653 A | 6/1988 | Lee et al. | |
| 4,760,024 A | 7/1988 | Lantero et al. | |
| 4,950,596 A | 8/1990 | Cheng et al. | |
| 5,279,948 A | 1/1994 | Pederson et al. | |
| 5,422,284 A | 6/1995 | Lau | |
| 5,837,365 A | 11/1998 | Chung | |
| 5,891,741 A | 4/1999 | Siiman et al. | |

OTHER PUBLICATIONS

Carlisle et al. Polymer-coated polyethylenimine/DNA complexes designed for triggered activation by intracellular reduction. The Journal of Gene Medicine 2003, vol. 6, pp. 337-344.*
Strehblow et al. Monoclonal antibody-polyethyleneimine conjugates targeting Her-2/neu or CD90 allow cell type-specific nonviral gene delivery. Journal of Controlled Release 2005, vol. 102, pp. 737-747.*
Gaidamakova et al. Molecular vehicle for target-mediated delivery of therapeutics and idagnostics. Journal of Controlled Release 2001, vol. 74, pp. 341-347.*
Instructions, PIERCE Biotechnology Inc., Rockville IL, 2005.*
Avrameas et al., "Communication to the Editors: Peroxidase labeled antibody and Fab conjugates with enhanced intracellular penetration," *Immunochemistry*, vol. 8, pp. 1175-1179 (1971).
Avrameas, S., "Coupling of Enzymes to Proteins with Glutaraldehyde: Use of the Conjugates for the Detection of Antigens and Antibodies," *Immunochemistry*, vol. 6, pp. 43-52 (1969).
Bai et al., "Poly(ethyleneimine)/Arginine-Glycine-Aspartic Acid Conjugates Prepared with N-Succinimidyl 3-(2-Pyridyldithio)propionate: An Investigation of Peptide Coupling and Conjugate Stability," *J. Poly. Sci: Part A: Poly Chem.*, vol. 42, pp. 6143-6154 (2004).

Boussif et al., "A versatile vector for gene and oglionucleotide transfer into cells in culture and in vivo: Polyethylenimine," *Proc. Natl. Acad. Sci USA.*, vol. 92, pp. 7297-7301 (1995).
Boussif et al., "Optimized galenics improve in vitro gene transfer with cationic molecules up to 1000-fold," *Gene Therapy*, 3, pp. 1074-1080 (1996).
Emi et al., "Coupling of the *Penicillium duponti* Acid Protease to Ethylene-Maleic Acid (1:1) Linear Copolymer: Preparation and Properties of the Water-Soluble Derivative," *Biochimica et Biophysica Acta*, Issue 445, pp. 672-682 (1976).
Godbey et al., "Poly(ethylenimine) and its role in gene delivery," *J. Control Release*, Issue 60, pp. 149-160 (1999).
Gonatas et al., "The Significance of Circulating and Cell-Bound Antibodies in Experimental Allergic Encephalomyelitis," *Am. J. Pathol.*, vol. 76, No. 3, pp. 529-544 (1974).
Johnson et al., "Preparation and Characterization of Some Derivatives of Poly(ethylenimine)," *Macromol.*, vol. 7, No. 2, pp. 149-153 (1974).
Johnson et al., "Specific Binding of Peroxidase-Labeled Myelin Basic Protein in Allergic Encephalomyelitis," *Proc. Nat. Acad. Sci.*, vol. 68, No. 11, pp. 2694-2698 (1971).
Kichler et al., "Polyethylenimines: A Family of Potent Polymers for Nucleic Acid Delivery," *Nonviral Vectors for Gene Therapy*, Ch. 9, Academic Press, San Diego, CA (1999).
Kircheis et al., "Design and gene delivery activity of modified polyethylenimines," *Adv. Drug Del. Rev.*, Issue 53, pp. 341-358 (2001).
Klibanov et al., "Preparation of Protein Conjugaytes with Chelate Polymers using Water-Soluble Carbodiimide and N-Hydroxysulphoxinimide," *Polymer Science U.S.S.R.*, vol. 31, No. 6, pp. 1284-1292 (1989).
Li et al., "Targeted gene delivery to pulmonary endothelium by anti-PECAM antibody," *Am. J. Physiol. Lung Cell. Mol. Physiol.*, Issue 278, pp. L504-L511 (2000).
Roberts et al., "Chemistry for peptide and protein PEGylation," *Adv. Drug Del. Rev.*, Issue 54, pp. 459-476 (2002).
Singh et al., "Starburst™ Dendrimers: Enhanced Performance and Flexibilty for Immunoassays," *Clin. Chem* vol. 40, No. 9, pp. 1845-1849 (1994).
Singh, P., "Terminal Groups in Starburst Dendrimers: Activation and Reactions with Proteins," *Bioconjugate Chem.*, vol. 9, No. 1, pp. 54-63 (1998).
Suh et al., "Conformational Flexibility of Poly(ethylenimine) and its Derivatives," *Bioorg. Chem.*, vol. 25, pp. 221-231 (1997).
Suh et al., "Ionization of Poly(ethylenimine) and Poly(allylamine) at Various pH's," *Bioorg. Chem.*, vol. 22, pp. 318-327 (1994).
Van Dijk-Wolthuis et al., "A Versatile Method for the Conjugation of Proteins and Peptides to Poly[2-(dimethylamino)ethyl methacrylate]," *Bioconjugate Chem.*, vol. 10, No. 4, pp. 687-692 (1999).
Wagner, E., "Ligand-Polycation Conjugates for Receptor-Targeted Gene Transfer," *Nonviral Vectors for Gene Therapy*, Ch. 10, Academic Press, San Diego, CA (1999).
Yazynina et al., "Immunoassay Techniques for Detection of the Herbicide Simazine Based on Use of Oppositely charged Water-Soluble Polyelectrolytes," *Anal. Chem.*, vol. 71, No. 16, pp. 3538-3543 (1999).

* cited by examiner

*Primary Examiner* — Shafiqul Haq
(74) *Attorney, Agent, or Firm* — Leydig, Voit & Mayer, Ltd.

(57) ABSTRACT

Water soluble, polyethylenimine polymers, conjugated to one or more active moiety are taught. Also taught are methods of making same, kits comprising same, and use of same in immunoassay systems.

27 Claims, 2 Drawing Sheets

STABLE WATER-SOLUBLE POLYETHYLENIMINE CONJUGATES AND METHODS OF USE THEREOF

FIELD OF INVENTION

This invention relates to the field of high sensitivity signal amplification in biomedical testing applications. This invention relates to the field of water-soluble polyethylenimine conjugates, such as polyethylenimine conjugated to glutaraldehyde, and methods of making and using same.

BACKGROUND OF THE INVENTION

1. Need for Signal Amplification

The need for high sensitivity testing methods is a constant quest in modern clinical and biomedical testing. High sensitivity testing allows for earlier diagnosis and therefore improved clinical care by narrowing the gap between diagnosis and treatment or better characterization of various research processes. Improved testing sensitivity can be achieved through several aspects of the testing parameters, one of which is the signal amplification.

Signal amplification is the use of specific detection methodologies to directly increase the signal in proportion to the amount of target in the reaction. Applicable reactions for signal amplification include analytical techniques that use an antibody molecule as a binding agent in detection and quantification of substances in a sample (known as immunoassays), and analytical techniques that employ nucleic acid (NA) probes for the same purpose (known as hybridization assays).

The basic principle behind signal amplification is the use of multiple reporter molecules combined with relatively small amount of detector molecules. In this way, for example in the case of an antibody detector molecule, it is possible to attach multiple reporter molecules such as horseradish peroxidase (HRP) or photoproteins per single binding partner. The result is amplified signal in comparison with standard non-amplified methods. Therefore, amplification methods entail the freedom of decreasing the amount of the binding reagent and hence the testing system noise which results in improved signal to noise ratio and therefore testing sensitivity.

Several approaches have been developed for signal amplification. One such approach is the use of dendrimer molecules. Dendrimers are small nanosize particles with multiple linking sites. Dendrimer molecules are synthesized with different polymerization methods, and the level of polymerization is stated as "generation" of dendrimers molecule (Clin. Chem. 40/9, 1845-1849 (1994)). Commercial entities such as Dade Behring (Deerfield, Ill.) are currently using the well established widely used Starburst dendrimers for signal amplification in automated immunoanalyzers. Dendrimers combine several important characteristics in accordance to charge density, molecular weight, number of primary groups for conjugation and well defined molecular shape (Clin. Chem. 40/9, 1845-1849 (1994)) However, dendrimers have their own limitations. Dendrimers drawbacks include high manufacturing cost, making them too expensive to manufacture and employ on a wide scale. Another drawback of dendrimers is that, although dendrimers are relatively small, due to their size, dendrimers suffer from steric hinderness of binding when used for signal amplification. Additionally, dendrimers suffer from an overly specialized linking chemistry. Further, for reasons of stability, dendrimers need to be supplied in organic solvents which can denature biological molecules—therefore pre-treatment steps are required before purchased dendrimers can be used. (Bioconjugate Chem. 9, 54-63, (1998))

Another approach developed for signal amplification is the conjugation of multiple reporter molecules to water-soluble polymers molecules which have multiple binding sites. These polymeric molecules are either natural (proteins, carbohydrate) or synthetic.

Conjugates of reporter molecules to water-soluble polymers are well documented. Several synthetic polymers with multiple linking groups have been employed for this purpose. In this methodology, the linking groups on any particular polymer frame could be the same or different. Linking groups comprising amine groups (U.S. Pat. No. 5,891,741)(Bioconjugate Chem., 10, 687-692, (1999)), thiol groups (Bioconjugate Chem., 10, 687-692, (1999)), carboxyl groups (Biochimica et Biophysica Acta, 445 672-682 (1976))(Polymer Science U.S.S.R. Vol. 31, No. 6, pp. 1284-1292, (1989)) (Anal. Chem., 71, 3538-3543(1999)) and hydroxyl groups (Advanced Drug Delivery Reviews 54 459-476 (2002)) are known. Polymers which carry one or multiple kinds of these linking groups have been reported and employed for various applications, including both amplification and non-amplification uses. Polymer groups comprising polycarboxyl polymer, native or modified polyethylene glycol polymers and polycarbohydrate polymers are the most commonly reported; some conjugates of the linking groups described herein and the polymer groups described herein are currently commercially available.

2. Conjugation Chemistry and Glutaraldehyde

Conjugation chemistry is a well developed field defining different approaches for linking two or more molecules with covalent bonds. The conjugation parameters usually depend on the type of cross-linking reagent, availability of reactive groups and the pK of these groups on molecules for conjugation. The use of different cross-linking reagents influences the characteristics of final conjugate as well as the amount of side products and intermediates.

In linking or conjugating various molecules with homogeneous reactive groups, the only known approach is to use homobifunctional cross-linking reagents. This approach usually results in high amount of intermediates and side homo-conjugate derivatives. In the case of linking or conjugating various molecules with heterogeneous reactive groups, heterobifunctional cross-linking reagents are employed which can minimize formation of homo-conjugates.

Gluteraldehyde (GA) is a widely used homobifunctional dialdehyde that is employed for creating chemical constructs of various molecules and it is the most commonly used cross-linking agent in conjugation chemistry. The chemical mechanism of GA cross-linking was introduced with the work of Avrameas in 1969 (Immunochemistry 6:43, (1969)).

Aldehyde groups on GA can react with epsilon amino groups of lysine residues of a protein to form Schiff base intermediates. The conjugation process usually involves activation step, followed by conjugation to a moiety of interest. Both the activation and conjugation steps are pH dependent. Activation with GA is optimal at acidic pH, while the conjugation step is optimal at alkaline pH due to ionization state of epsilon amino groups. (Bioconjugate Techniques, Academic Press, Elseiver (1996)) The conjugation of proteins with GA can be performed in single step (simultaneously) or in two steps (sequentially). One-step conjugation reactions are usually performed at pH range 6.8 to 10. (Immunochemistry 6:43, (1969); Proc. Natl Acad. Sci USA 68:2694, (1971)) In two step reactions the activation step is performed at pH 6.8 to 7.4, and the conjugation step is usually performed at pH range 7.5.to 9.5.

For stepwise reactions, usually there is intermediate step for removal of non-reacted glutaraldehyde by desalting or dialysis (Immunochemistry 8, 1175,(1971); Am. J. Pathol 76:529, 1974)).

After conjugation, Schiff base can be reduced with sodium borohydride or cyanoborohydride to give secondary amine and a stable linkage. However stable polymer or proteins conjugates can be formed by a process in which the reduction step is omitted. It has been suggested that the stability of such conjugates is due to the vinyl addition mechanism, which does not depend on formation of Schiff bases (Bioconjugate Techniques, Academic Press, Elseiver (1996)).

3. Polyethylenimine (PEI) and Conjugates Involving Solution-Phase Polyamines Polymers PEI is a synthetic positively charged polymer with numerous amine groups on the frame of the polymer, which provides the polymer with a high charge density. The basic unit of PEI is ethylamine and it has a backbone of two carbons followed by one nitrogen atom (Encyclopedia of Polymer Science and Engineering, Vol. 1, Wiley, New York, pp. 680-739 (1985.)). PEI's with various linking groups are available, including PEI's having primary, secondary, and tertiary amine groups on the surface of the polymer.

Two forms of PEI are commercially available—branched and linear. Both forms are obtainable by cationic polymerization with different monomers. Branched form is formed by polymerization of aziridine monomers by a chain-growth mechanism. During the polymerization, branch sites arise from specific interactions between two growing polymer molecules. In polymerization of the so-called "linear" form of PEI, 2-substituted 2-oxazoline monomer (rather than aziridine) is used. Polymerization of linear form is followed by hydrolysis of the polymer byproduct to yield linear PEI. Frequently, the linear form of PEI is also generated/formed via a chain-growth mechanism, but the reaction must take place at relatively low temperatures. Chaim-growth mechanism will construct linear PEI molecules with higher molecular weights (up to 25 000 Da) (Encyclopedia of Polymer Science and Engineering, Vol. 1, Wiley, New York, pp. 680-739 (1985)).

Because of the strong positive charge of PEI molecules, any further modification or conjugation to a PEI molecule has to be based on the characteristics of its protonation state. The branched form of PEI contains primary, secondary, and tertiary amines, in ratio 25%:50%:25%, each of them with the potential for protonation which is directly dependent to the microenvironment of every amino group (Bioorganic Chemistry 22, 318-327 (1994)). This gives PEI the attribute of serving as an effective buffer through a wide pH range.

A functional descriptor of PEI's protonation state is its pKa value, which has remained undefinable because thorough analysis of experimental data to obtain PEI's pKa value would require one to include an ionization constant for every amine group. With each PEI nitrogen having its own local environment influencing its protonation state, it is important to determine overall buffering capacity of PEI which directly correlates to pKa value. Experimentally determined pKa value of a particular PEI molecule is usually different from theoretically calculated values (most probably, because they are based on composite effects of amino groups on PEI molecule) Suh et al. reported the percentage of unprotonated nitrogen atoms of various PEI molecules, either modified or unmodified, at various pHs for two different concentrations. The data reported imply that the amount of PEI protonation depends, in part, on its concentration and modification. (Bioorganic Chemistry 22, 318-327 (1994); Bioorganic Chemistry 25, 221-231 (1997))

With a nitrogen atom appearing as one out of every three atoms in the PEI backbone, any benefits of branching and protonation state accumulate in relation to polymer size. Molecular weight of PEI varies from 2 kDa to 2000 kDa and it is usually reported as an average molecular weight. Branched and linear, modified and non-modified PEI polymers are commercially available in different molecular weights from various suppliers (Proc. Natl. Acad. Sci. USA 92 (16) 7297-7301(1995); Gene Ther. 3 1074-1080 (1996); Nonviral Vectors For Gene Therapy, Academic Press, San Diego, (1999)).

PEI is a well-known and utilized protein flocculating agent and it is commonly used for water and product purification (U.S. Pat. Nos. 5,387,365 and 5,422,284). Recently PEI has been used for biomedical purposes such as for gene delivery and enzyme immobilization due to its charge binding capabilities (Advanced Drug Delivery Reviews 53 341-358 (2001); Journal of Controlled Release 60 149-160 (1999)).

Use of PEI for biomedical applications, such as protein purification, solid phase synthesis and enzyme immobilization has been explored in the last few decades. Conjugation of the amino groups of the polycationic PEI polymer to various binding or functional moieties for preparing complex molecules has been documented. Covalent binding, by chemical crosslinking means, of enzyme, antibodies, and reporter molecules to PEI has been explored. This was mostly achieved through immobilization of PEI to solid surfaces and then conjugating the polymer reactive group (amino group or other induced reactive group) to another binding group of the molecule to be conjugated. The linking chemistry of the prior art have employed both homo- and hetero-bifunctional linkers.

PEI conjugates are commonly used for gene transfer due to the high positive charge of the polymer. One approach to achieve gene transfer relies on converting amino groups of PEI and a ligand molecule to thiol groups by SPDP reagent (N-succinimidyl-3-(2-pyridylthio)propionate). After SPDP modification, thiol groups are generated by reduction with dithiothreitol (DTT) (Am. J. Physiol. Lung Cell. Mol. Physiol., 278: L504-L511, (2000) ; Journal of Polymer Science: Part A: Polymer Chemistry, Vol. 42, 6143-6156 (2004)). The conjugation step is performed at neutral pH to induce disulfide bond formation between conjugating moieties. Alternatively, Traut's reagent (2-imminothiolane) can be used to convert primary amino groups on of the polymer to thiols, followed by conjugation to a reduced ligand (Journal of Immunological Method 289 37-45 (2004)) Another approach is the use of Dithiobis(succinimidylpropionate) (DSP) a homobifunctional NHS (N-hydroxysuccinimide) ester-based electrophilic cross-linking reagent and Dimethyl3,3-dithiobispropionimidate 2HCl (DTBP), which is a similar molecule. Both cross-linking reagents react with primary amines to form stable covalent linkages, and are constructed around a centrally located disulfide bond, which is cleavable with common reducing agents after conjugation. (Bioconjugate Chem. 12 989-994, (2001)) Recently, there was reports for successful conjugation of PEI molecule employing N-succinimidyl-4-(maleimidomethyl)cyclohexancarboxylate (SMCC) activation of primary amino groups on the polymer and stable covalent crosslinking with reduced or thiolated binding molecule. (Journal of Controlled Release 102 737-747 (2005)).

The conjugation of PEI with GA is a well known process useful for immobilization of enzymes (U.S. Pat. Nos. 4,386,158, 4,760,024, 5,279,948 and 4,749,653). Numerous patents and research publications described various conditions for PEI-GA activation and/or conjugation processes aimed at optimizing the activity of the construct, conjugation efficiency or particle size. The prior art methodology has employed solid phase conjugation protocols, either by design for the stated purpose or in order to minimize the effects of PEI charge on protein flocculation. None of the prior reported protocols have employed a solution phase protein conjugation process.

In the case of enzyme immobilization, some authors reported the use of charge density altered carboxy-methylated PEI (U.S. Pat. No. 4,950,596), but still the conjugation reaction takes place on the solid support of cell surface and the final conjugate is in the water insoluble, particle form.

A common character in all these constructs is the employment of a specific functional molecule conjugated to the polymer frame. Some applications also utilize the large positive charge or the polymer as an added feature of these constructs (Advanced Drug Delivery Reviews 53 341-358 (2001); Journal of Controlled Release 60 149-160 (1999)). However, although the high overall charge of PEI could be utilized beneficially, the same positive charge with a high charge density could be detrimental to both the conjugation process itself as well as the end-use process.

4. Failures with Previous Work of PEI Conjugation Attempts/Low Efficiency of Conjugations to PEI (Charge Density/Protonation Effects)

There are no reports on using GA chemistry with PEI polymer in liquid phase conjugation reactions to produce high molecular weight water-soluble conjugate. Most of the liquid phase reactions resulted in flocculation of the proteins and formation of colloidal solutions, which appear to be desired products in enzyme immobilization. If the desired product needs to be water soluble, the high positive charges of the polymer results in protein flocculation, which impede the conjugation efficiency and also the characteristics of the final product. As a flocculating agent, PEI charge density appears to be detrimental to the conjugation process as well as the solution stability of the formed constructs. Further, when GA is employed in the conjugation chemistry, the high capacity of PEI to scavenge GA requires the employment of large amount of GA, which is in and of itself detrimental to the protein functions as well as to the solution phase stability of the constructs.

In conjugation chemistry the protein structure and activity are vulnerable upon exposure and activation with GA. GA molecule is extremely reactive and usually creates internal cross-linking of the protein, which can lead to altered protein structure and function.

GA has been used for conjugation by a method using amino acid or amino group-containing molecules as additives in order to alter reactions between GA and the moiety to be conjugated for the purpose of preserving the activity of the conjugated moiety. For example, U.S. Pat. No. 4,681,843 describes employing a primary amine, glycine as an additive during conjugation of gluteraldehyde, and a protein molecule. U.S. Pat. No. 4,288,552 describes the use of polyethyleneimine as a moderating molecule for enzyme immobilization in order to maintain the enzyme activity. However, the final product described in both these disclosures was not a soluble conjugate.

In another approach, a solid support is used for all of the reactions of activation and conjugation when desired product needs to be directly immobilized. However, there are no reports or disclosure of using polyethylenimine conjugates to crosslink multiple functional moieties for further use in signal amplification. This is mainly due to the difficulty of keeping of polyethylenimine conjugates in water soluble form, due to the high positive charge density of polyethylenimine.

The present inventors have thus determined that it would be useful to produce high molecular weight, water-soluble GA-PEI conjugate, for use in enzyme immobilization or where signal amplification is required. It would also be useful to have stable, covalent conjugates of PEI and other functional molecules (such as GA). It would be useful to have a method of making such molecules in a liquid phase reaction.

SUMMARY OF THE INVENTION

The present invention encompasses a method for the synthesis of a stable, covalent conjugates of polyethylenimines and other functional molecules in liquid phase.

The present invention encompasses a step of charge alteration of polyethylenimines in order to both increase the conjugation efficiency as well as stability of the produced high molecular weight soluble conjugate.

The present invention discloses a process for conjugating one or more than one functional molecule of the same or of different kind to a polyethylenimine polymer to form a stable water soluble high molecular weight conjugate.

The present invention discloses a step of activating the polyethylenimine polymer with a heat-stabilized glutaraldehyde either before or after the charge alteration step.

According to one aspect of the present invention, the charge of a solution of polyethylenimine is altered by grafting a functional group on the polymer, activating the polymer with glutaraldehyde for a specific period of time, followed by adding the functional molecule to be conjugated.

According to another aspect of the present invention, a solution of polyethylenimine is activated with glutaraldehyde for a certain period of time; the charge of the polyethylenimine is altered by grafting a functional group on the polymer, followed by adding the functional molecule to be conjugated.

According to one aspect of the present invention is a method of conjugating a polyethylenimine polymer having a charge to one or more active moiety, comprising altering the charge on the polyethylenimine polymer with a charge modifying agent to form a charge-modified polyethylenimine, chemically activating the charge-modified polyethylenimine with an activating agent to form a chemically-activated polyethylenimine, and conjugating the chemically-activated polyethylenimine to the one or more active moiety. In one embodiment, the charge modifying agent can alter the charge on the polyethylenimine polymer by grafting a functional group to the polyethylenimine polymer. In a further embodiment, the functional group is a protein or a glycoprotein, for example, a carboxyl, methyl, or 2,3 dimethyl maleyl groups.

In a further embodiment, the charge modifying agent may have an anhydride functionality. For example, the charge modifying agent may be selected from the group consisting of succinic anhydride, acetic anhydride, 2,3 dimethyl maleic anhydride, maleic anhydride, citraconic anhydride, an NHS, and an sulfo-NHS derivative. The sulfo-NHS derivative may be sulfo-NHS acetate. The charge modifying agent may be succinic anhydride. The activating agent may be glutaraldehyde.

In a further embodiment, the chemical activation step results in an addition of one or more aldehyde groups to the charge-modified polyethylenimine.

In a further embodiment, multiple aldehyde groups may be added.

In a further embodiment, the polyethylenimine polymer may be a linear, or a branched polyethylenimine polymer. The polyethylenimine polymer may, for example, be Epomin 1050, Lupasol P, or Lupasol SK.

In a further embodiment, the polyethylenimine polymer is Lupasol-SK, the charge modifying agent is succinic anhydride, and the activating agent is gluteraldehyde.

In yet a further embodiment, 4996.5 to 16655 molar equivalents, for example, 14989 molar equivalents, of succinic anhydride may be used per molecule of Lupasol-SK.

In a further embodiment, the charge alteration step may take place from 5 to 15 minutes.

In a further embodiment, 20 to 120 mg, for example, 40 to 80 mg, of glutaraldehyde may be used per 12 mg of Lupasol-SK.

In a further embodiment, the chemical activation step may take place in a solution with a pH of between 4 and 7.4, for example, a solution with a pH of 4.0.

In yet a further embodiment, there may be less, or more, than one active moiety conjugated per molecule of polyethylenimine. For example, 0.35 to 4.2 mg of active moiety is conjugated per 0.125-6 mg of polyethylenimine polymer. Further, 1.4 mg to 4.2 mg of active moiety may be conjugated per 0.25 to 0.5 mg of polyethylenimine polymer, for example, 18.6 to 112 molar equivalents of active moiety may be conjugated per 0.5 mg of activated polyethylenimine polymer.

In a further embodiment, the active moiety may be a binding molecule, a reporter molecule, or a combination of the two. For example, a binding molecule such as streptavidin, avidin, glycoproteins, lectins, hormones, antigens, drugs, antibodies, antibody antigen binding fragments, RNA, DNA, or an oligonucleotide may be used. A reporter molecule such as photoproteins, enzymes or fluorophores may be used. Where an antibody is used, the antibody may be comprised of a mixture of a rabbit IgG and a mouse IgG, for example, in a ratio of rabbit IgG to mouse IgG of between 1-10 and 10-1. In another embodiment the active moiety is one or more IgG, streptavidin, or polystreptavidin.

According to another aspect of the present invention is an immunoassay method comprising diluting a conjugated polyethylenimine made as herein described in a liquid medium, adding a binding partner specific to the active moiety of said conjugated polyethylenimine, adding a signal generating system capable of generating a signal when the binding partner binds to the conjugated polyethylenimine, and measuring a signal generated from the signal generating system. In one embodiment, the liquid medium can be aqueous.

According to yet another aspect of the present invention is a compound comprising a polyethylenimine polymer conjugated to one or more active moiety, wherein such compound is soluble in water. In one embodiment, the polyethylenimine polymer is selected from the group consisting of Epomin 1050, Lupasol P, and Lupasol SK. In another embodiment, the active moiety is a binding molecule, a reporter molecule, or a combination of binding molecules and reporter molecules. In another embodiment, the binding molecule is streptavidin, avidin, glycoproteins, lectins, hormones, antigens, drugs, antibodies, antibody antigen binding fragments, RNA, DNA, or oligonucleotides. In another embodiment, the reporter molecules are photoproteins, enzymes or fluorophores.

In yet another embodiment, the active moiety can be an antibody, for example, a mixture of a rabbit IgG and a mouse IgG. The ratio of rabbit IgG to mouse IgG can be, for example, between 1-10 and 10-1.

In another embodiment, the active moiety is one or more IgG, streptavidin, or polystreptavidin.

Another aspect of the present invention is an immunoassay method comprising diluting a conjugated polyethylenimine made by the method described herein in a liquid medium, adding a binding partner specific to the active moiety of said conjugated polyethylenimine, adding a signal generating system capable of generating a signal when the binding partner binds to the conjugated polyethylenimine, and measuring a signal generated from the signal generating system. The liquid medium can, for example, be aqueous.

According to another aspect of the present invention is a compound comprising a polyethylenimine polymer conjugated to one or more active moiety, wherein such compound is soluble in water.

In another embodiment of the present invention, the polyethylenimine polymer can be Epomin 1050, Lupasol P, or Lupasol SK.

In another embodiment of the present invention, the active moiety can be binding molecules, reporter molecules, or a combination of binding molecules and reporter molecules. The binding molecule can be, for example, streptavidin, avidin, glycoproteins, lectins, hormones, antigens, drugs, antibodies, antibody antigen binding fragments, RNA, DNA, or oligonucleotides. The reporter molecule can be, for example, photoproteins, enzymes or fluorophores. The active moiety can be, for example, an antibody, such as mixture of a rabbit IgG and a mouse IgG. In one embodiment of the present invention, the ratio of rabbit IgG to mouse IgG is between 1-10 and 10-1. In another embodiment, the active moiety can be streptavidin or polystreptavidin.

One embodiment of the present invention is the compound as described herein wherein the polyethylenimine polymer is Lupasol-SK and the active moiety is polystreptavidin.

In one embodiment of the present invention, the polyethylenimine polymer conjugated to an active moiety is water soluble.

A further aspect of the present invention is a method of altering a charge on a polyethylenimine polymer having such a charge, comprising altering the charge of the PEI polymer using a compound with an anhydride functionality, wherein the charge is altered such that enough amino groups remain to allow further activation and conjugation of the polyethylenimine polymer.

A further aspect of the present invention is a kit comprising a water-soluble polyethylenimine polymer conjugated to an active moiety, and instructions for use in a binding assay.

A further aspect of the present invention is a kit comprising a water-soluble polyethylenimine polymer conjugated to an active moiety, a binding partner specific for the active moiety, and a signal generating system.

A further aspect of the present invention is a kit comprising a compound as described herein, combined with instructions for use of the compound in a binding assay.

A further aspect of the present invention is a kit comprising a water-soluble polyethylenimine polymer conjugated to an active moiety, a binding partner specific for the active moiety, and a signal generating system.

A further aspect of the present invention is the use of a compound as described herein in an immunoassay.

A further aspect of the present invention is an immunoassay method comprising diluting a conjugated polyethylenimine as described herein in a liquid medium, adding a binding partner specific to the active moiety of said conjugated polyethylenimine, adding a signal generating system capable of generating a signal when the binding partner binds to the conjugated polyethylenimine, and measuring a signal generated from the signal generating system. The liquid medium may, for example, be aqueous.

DETAILED DESCRIPTION OF THE INVENTION

Figure 1:
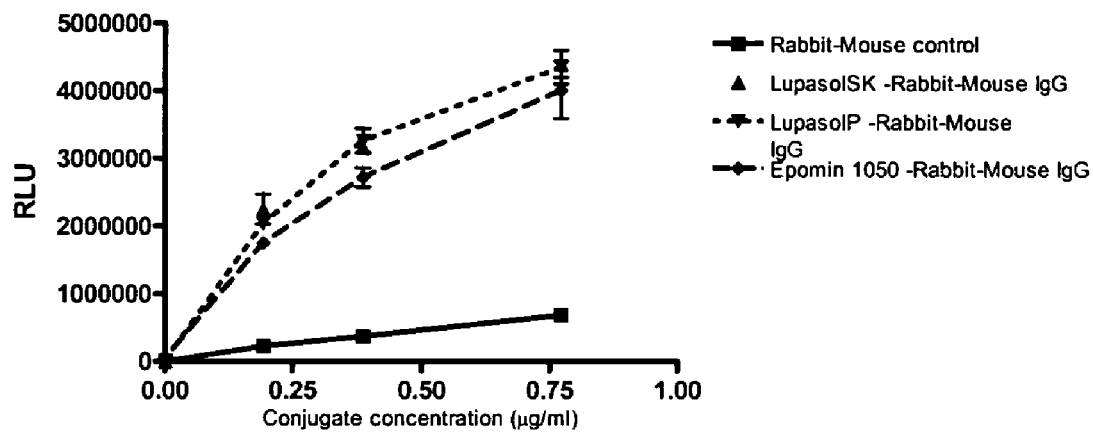
FIG. 1 shows signal amplification (measured in Relative Light Units) provided by three PEI-Rabbit-Mouse IgG conjugates (Lupasol-SK-Rabbit-Mouse IgG, Lupasol-P-Rabbit-Mouse IgG, and Epomin1050-Rabbit-Mouse IgG) as compared to a control Rabbit-Mouse conjugate.
Figure 2:
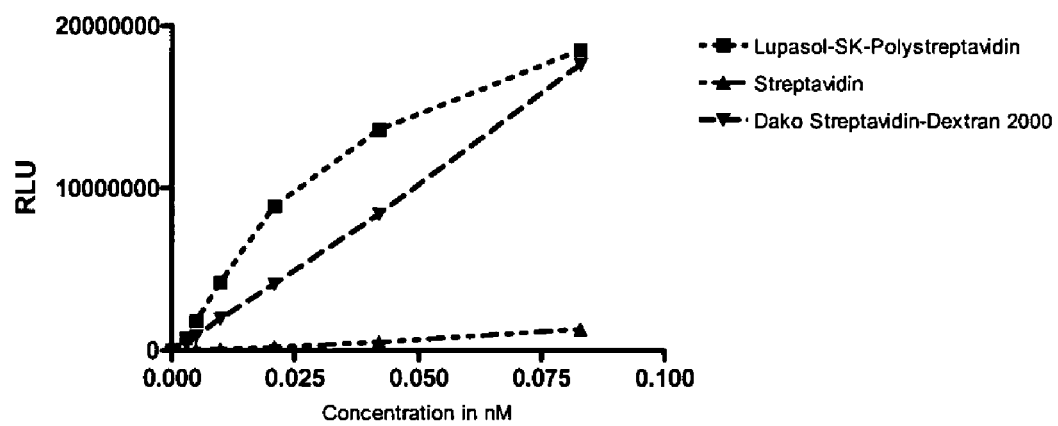
FIG. 2 shows signal amplification (measured in Relative Light Units) provided by a PEI-polystreptavidin conjugate (Lupasol-SK-polystreptavidin) as compared to Streptavidin and Dako Streptavidin-Dextran-2000 controls.
Figure 3:
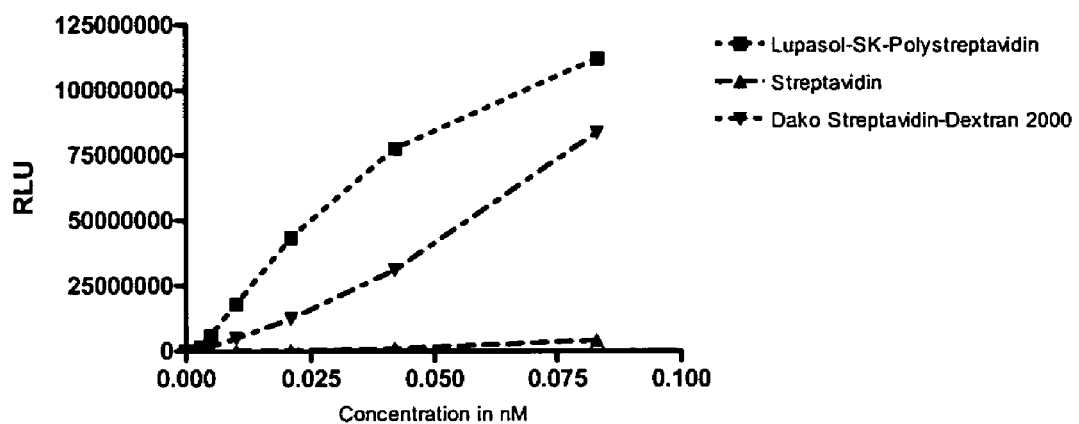
FIG. 3 shows signal amplification (measured in Relative Light Units) provided by a PEI-polystreptavidin conjugate (Lupasol-SK-polystreptavidin) as compared to Dako Streptavidin-Dextran 2000 and Streptavidin controls.
Figure 4:
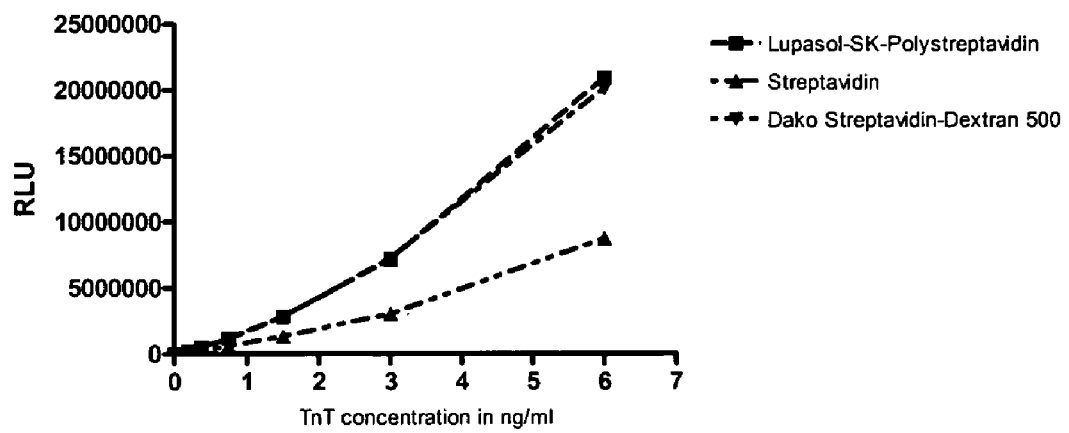
FIG. 4 shows signal amplification (measured in Relative Light Units) in a TroponinT test assay, provided by a PEI-streptavidin conjugate (Lupasol-SK-polystreptavidin), as compared to Dako Streptavidin-Dextran 500 and Streptavidin controls.

It has been found that polyethylenimine polymers can be successfully conjugated in liquid phase by chemical cross-linking means after charge alteration of the polyethylenimine polymers with modifying reagent. Treatment of the polyethylenimine polymer solution with the charge modifying agent results in the grafting of the functional group on the polymer that improves the conjugation process, stability of the produced conjugate as well as the non-specific adsorption and charge interaction of the produced conjugate. Further activation of the remaining amino groups is performed by a homobifunctional crosslinking reagent—glutaraldehyde.

Although not bound by theory, it is hypothesized that after charge alteration of the polyethylenimine polymers, the effect of microenvironment on remaining primary amino groups results in decreased pKa values and in higher activation efficiency with GA, as a result of higher amount of deprotonated primary amino groups at neutral or acidic pH values. The amount and deprotonation of the remaining amino groups is sufficient for adding multiple active aldehyde residues at neutral or acidic pH. The subsequent step of conjugation with functional moieties is performed at neutral pH values, in order to deprotonate amino groups in the case of a protein moiety and to increase stability of aldehyde derivate of the polyethylenimine.

We have discovered that altering the charge of the surface of the polyethylenimine by grafting a functional group to the polymer results in altering the functional moiety-polyethylenimine charge interaction. In case of a protein or glycoprotein, solution phase charge interaction of unmodified polyethylenimine usually results in protein flocculation or particle formation. Charge alteration of the polyethylenimine, before the activation step and prior to adding the protein to be conjugated, results in increasing the efficiency of conjugation probably by affecting the deprotonation of the remaining amino groups.

The result from the conjugation reaction is a complex soluble molecule with multiple binding moieties, with defined shape, formed by internal charge interactions between modified groups on the polyethylenimine, amino groups and any additional groups from binding moieties.

The conjugation method of the present invention includes the steps for preliminary alteration of the charge density of the polyethylenimine and subsequent chemical activation of the remaining amino groups, followed by conjugation to a moiety of interest. The method yields stable polyethylenimine conjugates that retain functionality of the conjugated moiety.

We have discovered that charge altered PEI's may be activated with glutaraldehyde and conjugated to an entity, yielding water-soluble constructs with preserved activity of the conjugated moiety. This is done by means of an activation step prior to adding of the molecule to be conjugated. The activation step allows one aldehyde group of the GA to react with an amino group of PEI polymer, while the remaining aldehyde group of GA is available for conjugation with a protein. This approach results in sparing the conjugated moiety from the detrimental potential of GA molecule.

PEI's are chemically modified with appropriate reagents, which react with one or more of the amino groups. Reaction with the charge altering reagent result in grafting a functional group, including, but are not limited to, carboxyl, methyl or 2,3 dimethylmaleyl groups on the surface of polyethylenimines. Preferably, multiple carboxyl groups are introduced to the polyethylenimine molecule. Examples of such modifying reagents include, but are not limited to, groups with anhydride functionality such as succinic anhydride, acetic anhydride, 2,3 dimethyl maleic anhydride, maleic anhydride, citraconic anhydride as well as some other NHS or sulfo-NHS derivates such as sulfo-NHS acetate. A preferred modifying reagent is succinic anhydride.

Polyethylenimines are chemically activated with glutaraldehyde to add at least one aldehyde group without additional purification steps after charge alternation. Preferably, multiple aldehyde groups are added to the polyethylenimine. Preferred activating reagent is glutaraldehyde.

Various polyethylenimines are employed in the current invention, including linear and branched polyethylenimines, and also polyethylenimines modified with functional groups other than the amine groups of the unmodified form. Further, the present invention employs polyethylenimines with different molecular weights, spanning a wide range from 20K-2000K. The conjugation process of the invention employs particular polyethylenimines depending on the intended final function to be achieved. Non-limiting examples of the polyethylenimines employed within the scope of the present invention include, Epomin1050, a 70 kDa molecule, Lupasol P, an 800 kDa molecule and Lupasol SK, a molecule of about 2000 kDa that is primarily employed for flocculation, due to the large molecular size.

In a preferred embodiment of the invention, a polyethoxylated polyamine, Lupasol-SK (BASF), is chemically modified with succinic anhydride, converting multiple primary amino groups to carboxyl groups, rendering it a polyamino-polycarboxyl polymer. Then, the polyamino-polycarboxyl modified Luposol SK is activated with glutaraldehyde. Subsequently, the aldehyde-activated polyamino-polycarboxyl polymer and deprotonated amino groups of the moiety to be conjugated are reacted under conditions that promote coupling to form a polyethylenimine-active moiety conjugate.

The charge alteration step of the polyethylenimines followed by activation allowed the formation of non-precipitated polymer solution with both positive and negative groups on its frame.

Accordingly, it is an object of the present invention to provide stable water soluble polyethylenimine conjugates where the polyethylenimine molecules are Epomin-1050/70 kDa, Lupasol-P/800 kDa or Lupasol-SK/2000 kDa. Experiments with different polyethylenimine molecules such as Epomin-1050/70 kDa, Lupasol-P/800 kDa or Lupasol-SK/2000 kDa revealed that the conjugation conditions could be varied to and tailored for the intended purpose of the final conjugate. In employing these conjugates for signal amplification, it has become clear that the higher molecular weight polyethylenimines are more suitable, as they carry larger number of functional molecules. Lupasol-SK, a very large 2000 kDa/polymer has provided the best results, in terms of number of molecules efficiently conjugated to the polymer frame. However, all yielded excellent results.

It is yet a further object of the present invention to provide a method for charge alteration of polyethylenimine polymers that retain enough amino groups for further activation with glutaraldehyde and further conjugation. According to the present invention, various compounds with anhydride functionality were employed to alter the charge of the polyethylenimine.

In order to obtain optimal ratios of charge alteration for the intended purpose of signal amplification, succinic anhydride was employed for charge alteration of Lupasol SK. Varying the molar ratios of the anhydride functional group and the Lupasol polymer demonstrate that a range between 4996.5 to 16655 molar equivalents of succinic anhydride per molecule of Lupasol SK worked well. Further, the period of modification was assessed before activation/quenching step and it revealed that a period of 5 and 15 min of charge alteration with 14989 molar equivalents of succinic anhydride to the polymer was sufficient to induce enough charge on the polymer frame for efficient conjugation with functional moieties.

Also, the sequence of the charge alteration step was assessed in relation to the activation/quenching step, e.g., charge alteration, then an activation step with glutaraldehyde or activation with glutaraldehyde followed by a step of quenching and charge alteration. Although the activation step could be carried out before the charge alteration step, much higher conjugation efficiency was achieved with an initial charge alteration step.

Various polymers were employed for assessing the efficiency of charge alterations and its effect on the conjugation efficiency. Amino group determination was done before and after charge alteration to assess its effect on conjugation efficiency. Before and after modification, amount of initial and remaining primary amino groups were evaluated by TNBS amino group titration in alkaline pH 8.0, 0.1M Borate buffer and 0.15 NaCl (Macromolecules 7, 149-153 (1974)). The efficiency of conjugation was evaluated by immunoassay reaction. Several polyethylenimine polymers were used for this purpose.

Experimental results, using the Lupasol SK polymer, revealed that with 14989 molar equivalents of succinic anhydride with reaction time of 15 min before the activation/quenching step has decreased charge density of Lupasol SK molecule 30-50 times based on the amount of the primary amino groups. Further conjugation with the product from above described charge alternation procedure, resulted in the most efficient conjugate with minimal background in immunoassay reactions based on the charge interactions. Varying the sequence of steps resulted in less efficient conjugation.

It is also an object of the present invention to provide a method for glutaraldehyde activation of primary amino groups of modified polyethylenimine polymers in order to incorporate multiple aldehyde residues prior to conjugation. The method of the invention discloses molar ratios that are ideal for the conjugation process with an amount of glutaraldehyde in the range of about 20 mg/33293 molar equivalents/, 40 mg/66587 molar equivalents/and 60 mg/99880 molar equivalents/for 12 mg of Lupasol SK. Further, the environment of this activation step was varied. An activation step of an environment of a pH of between 4 and 7.4 pH units worked well.

The effect of the micro-environment parameters on the efficiency of conjugation was evaluated by immunoassay reactions employing an array of antibodies conjugated to the polymer. A good molar ratio of glutaraldehyde to both the polymer and the molecule to be conjugated was determined by testing of function: the signal intensity, stability and ratio of specific signal and background values were assessed. An amount of 20-120 mg of glutaraldehyde produced efficient conjugation, with an optimal amount of between 40-80 mg of glutaraldehyde for 12 mg Lupasol-SK with pH for activation of 4.00.

It is also an object of the present invention to provide stable, water soluble polyethylenimine conjugates where the multiple functional moieties are conjugated by chemical cross-linking means to single polyethylenimine molecule for signal amplification purposes. We found that using between about 0.125-6 mg of polymer and between 0.35-4.2 mg of protein to be a functional protein mix. Although efficient conjugation was obtained within these ranges, stable and ideal conjugate was obtained when the ratio of 0.25 mg-0.5 mg of polymer and between 1.4 mg-4.2 mg of protein (a Rabbit and Mouse IgG mixture) was used and a ratio between 0.7 mg (18.6 molar equivalents) to 4.2 mg (112 molar equivalents) of protein for 0.5 mg of activated charge altered Lupasol-SK). Of course, it is likely that these conjugation parameters can be "scaled up", and that the ratios of protein to polymer are important in such a scale-up process.

The efficiency of conjugation was assessed by gel filtration chromatography; a Sephacryl-S300 column was employed. The efficiency of conjugation varied between 83-89%. The maximum yield of conjugate was achieved with 0.5 mg of Lupasol-SK and 112 molar equivalents of IgG mixture. Further, conjugation efficiency was confirmed in a functional manner by comparative immunoassays. Conjugation efficiency was 87% of the amount of binding moiety and 37% with respect to the amount of primary amino groups activated after charge alteration.

The final conjugates can be separated from the unreacted components of the reaction mixture by means commonly known to one skilled in the art. For example, the polyethylenimine-binding moiety conjugates generally will be substantially larger in size than either the polyethylenimine or binding moiety alone. They can therefore be purified by separation over a gel filtration chromatography column. Furthermore, polyethylenimine-binding moiety conjugates commonly will be substantially different in charge than either the polyethylenimine or binding moiety alone, therefore they may be separated by ion-exchange chromatography. Such separation techniques are well known in the art.

It is also an object of the present of the present invention to provide a method whereby binding moieties that contain one or more amino groups may be conjugated to a charge altered glutaraldehyde activated polyethylenimine such that the resulting conjugate retains solubility in water and buffers.

When the amount of glutaraldehyde used for conjugation is considered, the present invention provides much higher conjugation efficiency as compared to the same amount of glutaraldehyde used to conjugate two protein molecules in the absence of the charge altered polymer.

One application for the polyethylenimine functional moiety conjugate of the present invention is in the field of signal amplification including immunoassays, and hybridization assays that employ nucleic acid (NA) probes for the same purpose.

According to the present invention, PEI's may be conjugated with an array of moieties by covalent cross-linking means. These include:

Binding molecules, such as streptavidin/avidin, glycoproteins, lectins, hormones, antigens, drugs, antibodies and antigen binding fragments thereof, RNA, DNA, oligonucleotides, or any other selectively bindable molecules or compositions by chemical cross-linking means;

Reporter molecules, such as photoproteins, enzymes, fluorophores; or

A mix of the above functional molecules.

In a second aspect of the invention, we provide an immunoassay method for evaluation of conjugation efficiency and effect of the conjugation parameters on polyethylenimine-binding moiety conjugate. The functional immunoassay comprises preparing, in a liquid medium, dilutions of specific polyethylenimine-binding moiety conjugate carrying at least 1, but preferably, 2 molecules with different binding functionalities and subsequent addition of specific binding partners and other components of signal generating system in liquid medium, then measuring the generated signal from a signal system.

Preferred conjugated moieties are antibodies. The amounts of binding moieties in present invention used the principle for signal amplification described previously in the background of the invention, a mix of Rabbit IgG molecule and Mouse IgG molecule at different molar ratios (as considered one for capturing and one for reporting) was employed. The molar ratio of the 2 IgGs participating in conjugation was varied between 1-10 and 10-1 Rabbit IgG to Mouse IgG molecules, respectively. The polyethylenimine-binding moiety conjugates of the present invention may be used in a variety of binding assays.

In another format of the immunoassay utilized to evaluate the conjugates of the present invention with a charge alter polyethylenimine; a biotinylated antibody is employed utilizing a streptavidin conjugated to a reporter molecule. The reporter molecule was a chemiluminescent molecule and the efficiency of conjugation was assessed in relative light units (RLU) for serial dilutions of the conjugate.

The above-described conjugates are an example of the embodiments covered by the present invention and are not intended to restrict the scope of the invention.

The present invention will be better understood in light of the following specific examples.

EXAMPLES

Example 1

Conjugation of Rabbit-Mouse IgG Mix to Lupasol SK/2000 kDa (a) Preparation of PEI and Chemical Activation solutions A solution of 3.14 µM (6.28 mg/ml) of Lupasol SK was prepared in 0.1 M MOPS Buffer, pH 7.0 (final volume 1910 µl).

Succinic anhydride was dissolved in 99.99% DMSO immediately before use, final concentration is 1M (100 mg/ml).

(b) Charge Alteration Step

A total of 90 µL of the 1M solution of succinic anhydride (14989 molar equivalents) was mixed with the Lupasol SK solution and incubated for 15 min at room temperature without mixing (final concentration of the charge-altered Lupasol SK is 3 µM (6 mg/ml).

(c) Chemical Activation Step

Three hundred (300) microliters (99880 molar equivalents) of a 20% Glutaraldehyde solution was added to the solution of charge-altered Lupasol SK in 0.1M MOPS and the reaction mixture was incubated at room temperature without mixing for 1 hour.

After the 1 hour activation, the final volume was adjusted to 3000 µl [final concentration of 2 µM (4 mg/ml) Lupasol SK].

(d) Conjugation Step

A total of 125 µl of the aldehyde activated Lupasol SK polymer (at concentration of 2 µM) was added to 2000 µl of 0.1 M MOPS buffer (pH 7.0).

To the activated polymer solution, 37.33 molar equivalents [140 µl of a 66.66 µM (10 mg/ml) stock] of IgG mixture (rabbit/mouse IgG at 1:5 molar ratio) in 0.01M Phosphate buffer was added (the final concentration of charge altered, aldehyde activated polymer and binding moieties was 0.110 µM (0.220 mg/ml) Lupasol-SK, and 4.121 µM (0.618 mg/ml) Rabbit-Mouse IgG mix).

Conjugation was carried out for 16-20 hours at room temperature with slow shaking.

(e) Purification Step

The conjugate was purified with an ion-exchange chromatography (HiTrap HiTrap CM-Cellulose FF FF column, Amersham Pharmacia).

Example 2

Conjugation of a Rabbit-Mouse IgG Mix to Charge-Altered Lupasol P/800 kDa (a) Preparation of PEI and Chemical Activation Solutions A Solution of 8.66 µM (6.93 mg/ml) of Lupasol P was prepared by diluting a stock solution in 0.1 M MOPS Buffer pH 7.0 (final volume 1850 µl).

A solution of succinic anhydride was prepared by the method of Example 1.

(b) Charge Alteration Step

A total of 150 µL (9993 molar equivalents) of the succinic anhydride solution was added to the Lupasol P polymer solution and incubated for 15 min.

(c) Chemical Activation Step

Three hundred microliter (300 µl) (39952 eq.) of a 20% Glutaraldehyde solution was added to the charge altered Lupasol P polymer solution and the reaction mixture was incubated for 1 hour at room temperature, without mixing;

After 1 hour activation, final volume of reaction mixture was adjusted to 3000 ρl [final concentration of 5 µM (4 mg/ml) Lupasol P];

(d) Conjugation Step

A total of 125 µl of the aldehyde activated, charge altered Lupasol P polymer (at concentration of 5 µM) was added to 2000 µl of 0.1 M MOPS buffer (pH 7.00).

An 14.99 molar equivalents of IgG mixture used in example 1 [140 µl of a 10 mg/ml stock] in 0.01M Phosphate buffer was added [the final concentration of charge altered, aldehyde activated polymer and binding moieties was 0.275 uM (0.220 mg/ml) Lupasol-P and 4.121 µM (0.618 mg/ml) Rabbit-Mouse IgG mix].

Conjugation was carried out for 16-20 hours with slow shaking at room temperature.

(e) Purification Step

The conjugation mixture was purified with an ion-exchange chromatography (HiTrap CM-Cellulose FF column by Amersham Pharmacia).

Example 3

Conjugation of Rabbit-Mouse IgG Mix to Epomin-1050/70 kDa (a) Preparation of PEI and Chemical Activation Solutions A solution of 99 µM (6.93 mg/ml) Epomin-1050 was prepared by diluting a 5% stock solution with 0.1 M MOPS Buffer pH 7.0 (final volume 1850 µl).

A succinic anhydride solution was prepared according to the method described in Example 1.

(b) Charge Alteration Step

A total of 150 µL (874.4 molar equivalents) of succinic anhydride solution was added to the polymer solution and charge alteration was carried out for 15 min at room temperature without mixing.

(c) Chemical Activation Step

Three hundred (300) microliter (3496 molar equivalents) of a 20% Glutaraldehyde solution was added to the charge altered Epomin-1050 polymer solution and the reaction mixture was incubated for 1 hour at room temperature, without mixing;

After 1 hour activation, final volume of reaction mixture was adjusted to 3000 µl [final concentration of 57.14 µM (4 mg/ml) Epomin-1050].

(d) Conjugation Step

A total of 125 µl of the aldehyde activated, charge altered Epomin-1050 polymer (at concentration of 5 µM) was added to 2000 µl of 0.1 M MOPS buffer (pH 7.0).

An 1.31 molar equivalents (140 µl) of IgG mixture used in example 1 [from 10 mg/ml stock] in 0.01M Phosphate buffer was added [final concentration of charge-altered, aldehyde-activated polymer and binding moieties was 3.14 µM (0.220 mg/ml) Epomin-1050, and 4.121 µM (0.618 mg/ml) Rabbit-Mouse IgG mix].

Conjugation reaction was incubated with slow-shaking at room temperature for 16-20 hours.

(e) Purification Step

The conjugation mixture was purified by using an ion-exchange chromatography (HiTrap CM-Cellulose FF column, Amersham Pharmacia).

Example 4

Conjugation of Streptavidin to Lupasol SK/2000 kDa/

(a) Preparation of PEI and Chemical Activation Solutions

A solution of 3.14 µM (6.28 mg/ml) of Lupasol SK was prepared in 0.1 M MOPS Buffer, pH 7.0 (final volume 1910 µl).

Succinic anhydride was dissolved in 99.99% DMSO immediately before use, final concentration is 1M (100 mg/ml).

(b) Charge Alteration Step

A total of 90 µL of the 1M solution of succinic anhydride (14989 molar equivalents) was mixed with the Lupasol SK solution and incubated for 15 min at room temperature without mixing (final concentration of the charge-altered Lupasol SK is 3 µM (6 mg/ml).

(c) Chemical Activation Step

Three hundred (300) microliters (99880 molar equivalents) of a 20% Glutaraldehyde solution was added to the solution of charge-altered Lupasol SK in 0.1M MOPS and the reaction mixture was incubated at room temperature without mixing for 1 hour.

After the 1 hour activation, the final concentration was adjusted to 3000 µl [final concentration of 2 µM (4 mg/ml) Lupasol SK].

(d) Conjugation Step

A total of 125 µl of the aldehyde activated Lupasol SK polymer (at concentration of 2 µM) was added to 2000 µl of 0.1 M MOPS buffer (pH 7.0).

To the activated polymer solution, 37.33 molar equivalents [140 µl of a 66.66 µM (10 mg/ml) stock] of streptavidin in 0.01M Phosphate buffer was added (the final concentration of charge altered, aldehyde activated polymer and streptavidin was 0.055 µM (0.111 mg/ml) Lupasol-SK, and 6.33 µM (0.380 mg/ml) Streptavidin).

Conjugation was carried out for 16-20 hours at room temperature with slow shaking.

(e) Purification Step

The conjugate was purified with an ion-exchange chromatography (HiTrap HiTrap CM-Cellulose FF FF column, Amersham Pharmacia).

Example 5

Comparative Bioluminescent Linked Immunosorbent Assay Testing Procedure Employing Lupasol SK/2000 kDa/, Lupasol P/800 kDa/, Epomin-1050/70 kDa/Conjugated to Rabbit-Mouse IgG Mix One hundred (100) µl of 8 µg/ml Goat Anti-Rabbit IgG in 0.1 M Carbonate-Bicarbonate buffer pH 9.6 per well was coated to a solid support (Greiner Maximum Binding, flat bottom White*) for 2 hours at room temperature. After coating, the plate was washed three times with 200 µl of Phosphate Buffered Saline (0.0074M $Na_2HPO_4$, 0.0025M $KH_2PO_4$, 0.25M NaCl, pH 7.4). The Plate was then blocked for 1 hour with 200 µl of 1% Casein in 0.01 M Phosphate Buffered Saline (0.0074 M $Na_2HPO_4$, 0.0025 M $KH_2PO_4$, 0.25 M NaCl). After blocking, the plate was washed three times with 200 µl of Phosphate Buffered Saline (0.0074M $Na_2HPO_4$, 0.0025M $KH_2PO_4$, 0.25M NaCl, 0.005M EDTA, 0.005M Mercaptoethanol, 0.25% Tween 20, 0.005% Pluronic F 68, pH 7.4).

One hundred (100) µl of serial dilutions of the test conjugate (Lupasol SK/2000 kDa/, Lupasol P/800 kDa/, Epomin-1050/70 kDa conjugated to Rabbit-Mouse IgG mix) and control (a Rabbit-Mouse direct conjugate) in MES buffer (0.1M MES, 0.25 M NaCl, 0.005 M EDTA, 0.25% Tween 20, 0.005% Pluronic F68, 0.1% Casein, 1% Human Serum, pH 7.0) in serial dilutions from 0.76 µg/ml to 0.00019 µg/ml total protein were prepared and applied to each well, in duplicates. After 30 min. incubation at room temperature with moderate shaking, plates were washed three times with 200 µl of Phosphate Buffered Saline (0.0074M $Na_2HPO_4$, 0.0025M $KH_2PO_4$, 0.25M NaCl, 0.005M EDTA, 0.005M Mercaptoethanol, 0.25% Tween 20, 0.005% Pluronic F 68, pH 7.4).

One hundred (100) µl of biotinylated Goat Anti-Mouse secondary antibody (concentration of 3 µg/ml in MES buffer (0.1M MES, 0.25 M NaCl, 0.005 M EDTA, 0.25% Tween 20, 0.005% Pluronic F68, 0.1% Casein, 1% Human Serum, pH 7.0) was added to each well and incubated for 30 min at room temperature with moderate shaking, followed by washing three times with 200 μl of Phosphate Buffered Saline (0.0074M $Na_2HPO_4$, 0.0025M $KH_2PO_4$, 0.25M NaCl, 0.005M EDTA, 0.005M Mercaptoethanol, 0.25% Tween 20, 0.005% Pluronic F 68, pH 7.4).

One hundred (100) μl of a Streptavidin-Obelin conjugate at a final concentration of 1 μg/ml in MES buffer (0.1M MES, 0.25 M NaCl, 0.005 M EDTA, 0.25% Tween 20, 0.005% Pluronic F 68, 0.1% Casein, 1% Human Serum, pH 7.0) was applied to each well and incubated for 20 min at room temperature with moderate shaking, followed by another washing step (three times with 200 μl of Phosphate Buffered Saline (0.0074M $Na_2HPO_4$, 0.0025M $KH_2PO_4$, 0.25M NaCl, 0.005M EDTA, 0.005M Mercaptoethanol, 0.25% Tween 20, 0.005% Pluronic F 68, pH 7.4).

The chemiluminescent reaction was then triggered with 50 μl 0.1M 100 mM $CaCl_2$, 50 mM MES pH 6.0. The emitted light was detected employing SeaLite strip luminometer, and standardized to Relative Light Units. Test results were tabulated in Table 1.

Results

TABLE 1

Average results, measured in Relative Light Units, from duplicate testing: Comparative Bioluminescent Linked Immunosorbent Assay Testing Procedure employing Lupasol SK/2000 kDa/, Lupasol P/800 kDa/, Epomin-1050/70 kDa/conjugated to Rabbit-Mouse IgG mix

| Concentration (μg/ml) | LupasolSK - Rabbit-Mouse IgG mix conjugate | LupasolP - Rabbit-Mouse IgG mix conjugate | Epomin 1050 - Rabbit-Mouse IgG mix conjugate | Rabbit-Mouse IgG conjugate (Control) |
|---|---|---|---|---|
| 0.773 | 4.39E+06 | 4.35E+06 | 4.01E+06 | 6.87E+05 |
| 0.3865 | 3.16E+06 | 3.26E+06 | 2.72E+06 | 3.67E+05 |
| 0.19325 | 2.25E+06 | 2.03E+06 | 1.75E+06 | 2.22E+05 |
| 0 | 4.37E+04 | 4.37E+04 | 4.37E+04 | 4.37E+04 |
| Conjugate Background | 5.95E+03 | 1.62E+04 | 5.26E+04 | 2.97E+03 |

Example 6

Comparative Immunoassay Employing Lupasol-SK—Polystreptavidin (SP061P), Streptavidin, DAKO Streptavidin-Dextran 2000 Utilizing a Bioluminescent Linked Immunosorbent Assay with Detector Biotin-Obelin One hundred (100) μl of 0.6 μg/ml biotinylated Goat IgG in 0.1 M Carbonate-Bicarbonate buffer pH 9.6 was coated to a solid support (Greiner Maximum Binding, White* flat bottom plate) and incubated for 2 hours at room temperature. The plate was then washed three times with 200 μl Phosphate Buffered Saline (0.0074 M $Na_2HPO_4$, 0.0025 M $KH_2PO_4$, 0.25 M NaCl, pH 7.4).

Wells were blocked for 1 hour with 200 μl, 1% Casein in Phosphate Buffered Saline (0.0074 M Na2HPO4, 0.0025 M $KH_2PO_4$, 0.25 M NaCl, pH 7.4. After blocking, the plate was again washed three times with 200 μl of Phosphate Buffered Saline (0.0074M $Na_2HPO_4$, 0.0025M $KH_2PO_4$, 0.25M NaCl, 0.005M EDTA, 0.005M Mercaptoethanol, 0.25% Tween 20, 0.005% Pluronic F 68, pH 7.4).

One hundred (100) μl of test conjugates (SP061P, Dako Streptavidin-Dextran 2000 and Streptavidin control) in serial dilutions from 0.083 nM to 0.003 nM prepared in MES buffer (0.05M MES, 0.25M NaCl, 0.005M EDTA, 0.25% Tween 20, 0.005% Pluronic F68, 0.1% Casein, 1% Human Serum, pH 7.0) were added to each well, in duplicates. (Note: Concentrations were based on protein concentration and average molecular weight of conjugates)

After 30 min. incubation at room temperature with moderate shaking, plate was washed again (three times with 200 μl of Phosphate Buffered Saline (0.0074M $Na_2HPO_4$, 0.0025M $KH_2PO_4$, 0.25M NaCl, 0.005M EDTA, 0.005M Mercaptoethanol, 0.25% Tween 20, 0.005% Pluronic F 68, pH 7.4)).

One hundred (100) μl of 1 μg/ml Biotinylated Obelin conjugate was prepared in MES buffer (0.05M MES, 0.25M NaCl, 0.005M EDTA, 0.25% Tween 20, 0.005% Pluronic F 68, 0.1% Casein, 1% Human Serum, pH 7.0) and applied to each well in duplicates. After 30 min. incubation at room temperature with moderate shaking, plate was washed as before and the chemiluminescent reaction was triggered with 50 μl 0.1M 0.1 M $CaCl_2$, 0.05 M MES pH6.0. The emitted light was detected employing Luminoskan Ascent luminometer. Integration time was 30 s.

Results

TABLE 2

Average results, measured in Relative Light Units, from duplicate testing: Comparative immunoassay employing Lupasol-SK - polystreptavidin (SP061P), Streptavidin, DAKO Streptavidin-Dextran 2000 utilizing a Bioluminescent Linked Immunosorbent Assay with detector Biotin-Obelin

| Concentration in nM | Lupasol-SK-Polystreptavidin | Streptavidin Control | Dako Streptavidin-Dextran 2000 |
|---|---|---|---|
| 0.083 | 1.85E+07 | 1.30E+06 | 1.76E+07 |
| 0.042 | 1.36E+07 | 5.05E+05 | 8.39E+06 |
| 0.021 | 8.88E+06 | 2.07E+05 | 4.09E+06 |
| 0.01 | 4.20E+06 | 7.67E+04 | 1.96E+06 |
| 0.005 | 1.83E+06 | 3.37E+04 | 8.78E+05 |
| 0.003 | 7.68E+05 | 1.73E+04 | 3.83E+05 |
| 0 | 1.29E+03 | 4.89E+03 | 3.74E+03 |
| Conjugate background | 2.75E+03 | 2.81E+03 | 4.04E+03 |

Example 7

Comparative Immunoassay Employing Lupasol-SK—Polystreptavidin (SP061P), Streptavidin, DAKO Streptavidin-Dextran 2000. Testing Procedure Bioluminescent Linked Immunosorbent Assay Detector Luciferase-Obelin One hundred (100) μl of 0.6 μg/ml biotinylated Goat IgG in 0.1 M Carbonate-Bicarbonate buffer pH 9.6 was coated to a solid support (Greiner Maximum Binding, White* flat bottom) and incubated for 2 hours at room temperature. After coating, the plate was washed three times with 200 μl of Phosphate Buffered Saline (0.0074 M $Na_2HPO_4$, 0.0025 M $KH_2PO_4$, 0.25 M NaCl, pH 7.4).

Wells were blocked for 1 hour with 200 μl, 1% Casein in Phosphate Buffered Saline (0.0074 M Na2HPO4, 0.0025 M $KH_2PO_4$, 0.25 M NaCl, pH 7.4). After blocking, the plate was again washed three times with 200 μl of Phosphate Buffered Saline (0.0074M $Na_2HPO_4$, 0.0025M $KH_2PO_4$, 0.25M NaCl, 0.005M EDTA, 0.005M Mercaptoethanol, 0.25% Tween 20, 0.005% Pluronic F 68, pH 7.4).

One hundred (100) μl of test conjugates (SP061P, Dako Streptavidin-Dextran 2000 and Streptavidin control) in serial dilutions from 0.083 nM to 0.003 nM prepared in MES buffer (0.05M MES, 0.25M NaCl, 0.005M EDTA, 0.25% Tween 20, 0.005% Pluronic F68, 0.1% Casein, 1% Human Serum, pH 7.0) was added to each well in duplicates. (Note: Concentrations were based on protein concentration and average molecular weight of conjugates). Plates were incubated for 30 minutes at room temperature with moderate shaking, then washed as before (three times with 200 μl of Phosphate Buffered Saline (0.0074M $Na_2HPO_4$, 0.0025M $KH_2PO_4$, 0.25M NaCl, 0.005M EDTA, 0.005M Mercaptoethanol, 0.25% Tween 20, 0.005% Pluronic F 68, pH 7.4)).

One hundred (100) μl of 1 μg/ml Biotinylated Luciferase (Bio-Luc T) conjugate was prepared in 0.01 M PBS buffer (0.0074M $Na_2HPO_4$, 0.0025M $KH_2PO_4$, 0.25M NaCl, 0.005M EDTA, 0.25% Tween 20, 1% Casein, 1% Human Serum, pH 7.0) and applied to each well. The plates were incubated at room temperature for 30 minutes with moderate shaking, then was washed as before. To each well was then added 50 μl substrate buffer: 0.05 M Phosphate buffer, 0.0003M EDTA, 0.04M mercaptoethanol, 0.001M ATP and 0.001 M D-Luciferin.

The chemiluminescent reaction was triggered with 50 μl 0.05M $MgCl_2$, in $H_2O$, the emitted light was detected employing Luminoskan Ascent luminometer. Integration time was 30 seconds.
Results

TABLE 3

Average results, measured in Relative Light Units, from duplicate testing: Comparative immunoassay employing Lupasol-SK - polystreptavidin (SP061P), Streptavidin, DAKO Streptavidin-Dextran 2000. Testing procedure Bioluminescent Linked Immunosorbent Assay detector Luciferase-Obelin

| Concentration in nM | Lupasol-SK-Polystreptavidin | Streptavidin | Dako Streptavidin-Dextran 2000 |
|---|---|---|---|
| 0.083 | 1.12E+08 | 4.13E+06 | 8.35E+07 |
| 0.042 | 7.75E+07 | 9.71E+05 | 3.11E+07 |
| 0.021 | 4.35E+07 | 2.55E+05 | 1.24E+07 |
| 0.01 | 1.80E+07 | 5.79E+04 | 4.91E+06 |
| 0.005 | 5.97E+06 | 5.59E+04 | 1.77E+06 |
| 0.003 | 1.70E+06 | 4.51E+04 | 5.65E+05 |
| 0 | 1.16E+05 | 4.40E+04 | 3.93E+04 |
| Detector background | 6.68E+04 | 2.60E+04 | 2.83E+04 |

Example 8

Comparative Immunoassay for TroponinT Employing Amplification Step with Lupasol-SK—Polystreptavidin (SP061P) and DAKO Streptavidin-Dextran 500 Versus Streptavidin, Testing Procedure Bioluminescent Linked Immunosorbent Assay with Detector Biotin-Obelin One hundred (100) μl of 4 μg/ml MAK<TN-T>M11.7 monoclonal antibody in 0.1 M Carbonate-Bicarbonate buffer pH 9.6 was coated to a solid support (Greiner Maximum Binding, White* flat bottom) and incubated for 2 hours at room temperature. The plates were then washed three times with 200 μl Phosphate Buffered Saline (0.0074 M $Na_2HPO_4$, 0.0025 M $KH_2PO_4$, 0.25 M NaCl, pH 7.4).

Wells were blocked for 1 hour with 200 μl, 1% Casein in Phosphate Buffered Saline (0.0074 M Na2HPO4, 0.0025 M $KH_2PO_4$, 0.25 M NaCl, pH 7.4), then washed three times with 200 μl of Phosphate Buffered Saline (0.0074M $Na_2HPO_4$, 0.0025M $KH_2PO_4$, 0.25M NaCl, 0.005M EDTA, 0.005M Mercaptoethanol, 0.25% Tween 20, 0.005% Pluronic F 68, pH 7.4).

Fifty (50) μl of MAK<TN-T>M11.7 with concentration 8 ug/ml in 2×MES buffer (0.05M MES, 0.25M NaCl, 0.005M EDTA, 0.25% Tween 20, 0.05% Pluronic F127, 0.4% Casein, 20 □g/ml Mouse IgG, pH 7.0) was added to each well in duplicates. Immediately fifty (50) μl of TroponinT antigen in serial dilutions from 3 to 0.094 ng/ml in Human Serum, 0.005M EDTA was also added to each well in duplicates. After 10 min. incubation at room temperature with vigorous shaking, plate was washed as before (three times with 200 μl of Phosphate Buffered Saline (0.0074M $Na_2HPO_4$, 0.0025M $KH_2PO_4$, 0.25M NaCl, 0.005M EDTA, 0.005M Mercaptoethanol, 0.25% Tween 20, 0.005% Pluronic F 68, pH 7.4)).

Separately, one hundred (100) μl 2.5 μg/ml of SP061P, Dako Streptavidin-Dextran 500 and Streptavidin control were prepared in MES buffer (0.05M MES, 0.25M NaCl, 0.005M EDTA, 0.25% Tween 20, 0.005% Pluronic F 68, 0.1% Casein, 1% Human Serum, pH 7.0) and mixed in tubes with detector molecule dilution.

Accordingly, one hundred (100) μl 1.5 μg/ml of Obelin-Biotin was prepared in MES buffer (0.05M MES, 0.25M NaCl, 0.005M EDTA, 0.25% Tween 20, 0.005% Pluronic F 68, 0.1% Casein, 1% Human Serum, pH 7.0) and applied to previously prepared polymer dilutions.

After 15 min. incubation at room temperature with no shaking, the 100 μl from the mixture in the tubes was transferred to each well in duplicates. After 15 min. incubation at room temperature with moderate shaking, plate was washed as before and the chemiluminescent reaction was triggered with 50 μl 0.1 M 0.1 M $CaCl_2$, 0.05 M MES pH6.0; the emitted light was detected employing Luminoskan Ascent luminometer. Integration time was 30 s.

Results

TABLE 4

Average results, measured in Relative Light Units, from duplicate testing: Comparative immunoassay for TroponinT employing amplification step with Lupasol-SK - polystreptavidin (SP061P) and DAKO Streptavidin- Dextran 500 versus Streptavidin, Testing procedure Bioluminescent Linked Immunosorbent Assay with detector Biotin-Obelin

| TnT concentration in ng/ml | Lupasol-SK-Polystreptavidin | Streptavidin | Dako Streptavidin-Dextran 500 |
|---|---|---|---|
| 6 | 2.09E+07 | 8.73E+06 | 2.01E+07 |
| 3 | 7.15E+06 | 3.05E+06 | 7.23E+06 |
| 1.5 | 2.85E+06 | 1.34E+06 | 2.83E+06 |
| 0.75 | 1.22E+06 | 6.05E+05 | 1.16E+06 |
| 0.375 | 5.22E+05 | 2.22E+05 | 5.06E+05 |
| 0.188 | 2.49E+05 | 1.14E+05 | 2.39E+05 |
| 0 | 3.15E+04 | 2.77E+04 | 2.38E+04 |
| Detector background | 1.20E+04 | 3.39E+04 | 9.31E+03 |

We claim:

1. A method of conjugating a polyethylenimine polymer having a charge to one or more active moieties, comprising:
   (a) altering the charge on the polyethylenimine polymer with a charge modifying agent to form a charge-modified polyethylenimine;
   (b) chemically activating the charge-modified polyethylenimine with an activating agent to form a chemically-activated polyethylenimine; and
   (c) conjugating the chemically-activated polyethylenimine to one or more active moieties selected from the group consisting of streptavidin, polystreptavidin, avidin, glycoproteins, lectins, hormones, antigens, drugs, antibodies, antibody antigen binding fragments, RNA, DNA, oligonucleotides, photoproteins, enzymes, fluorophores, and combinations thereof;
   wherein the charge modifying agent has an anhydride functionality and alters the charge on the polyethylenimine polymer by grafting a functional group to the polyethylenimine polymer, said functional group not participating in steps (b) and (c), and wherein the activating agent is glutaraldehyde.

2. The method of claim 1 wherein the charge modifying agent is succinic anhydride.

3. The method of claim 1 wherein the chemical activation step results in an addition of one or more aldehyde groups to the charge-modified polyethylenimine.

4. The method of claim 1 wherein the polyethylenimine polymer is a branched polyethylenimine polymer.

5. The method of claim 1 wherein the polyethylenimine polymer is selected from the group consisting of Epomin 1050, Lupasol P, and Lupasol SK.

6. The method of claim 1 wherein the polyethylenimine polymer is Lupasol SK.

7. The method of claim 1 wherein the polyethylenimine polymer is Lupasol-SK, and the charge modifying agent is succinic anhydride.

8. The method of claim 7 wherein 4996.5 to 16655 molar equivalents of succinic anhydride is used per molecule of Lupasol-SK.

9. The method of claim 8 wherein the charge alteration step takes place for 5 to 15 minutes.

10. The method of claim 8 wherein 14989 molar equivalents of succinic anhydride is used per molecule of Lupasol-SK.

11. The method of claim 7 wherein 20 to 120 mg of glutaraldehyde is used per 12 mg of Lupasol-SK.

12. The method of claim 11 wherein 40 to 80 mg of glutaraldehyde is used per 12 mg of Lupasol-SK.

13. The method of claim 7 wherein the chemical activation step takes place in a solution with a pH of between 4 and 7.4.

14. The method of claim 13 wherein the chemical activation step takes place in a solution with a pH of 4.

15. The method of claim 1 wherein there is more than one active moiety conjugated per molecule of polyethylenimine.

16. The method of claim 15 wherein 0.35 to 4.2 mg of active moiety is conjugated per 0.125-6 mg of polyethylenimine polymer.

17. The method of claim 16 wherein 1.4 mg to 4.2 mg of active moiety is conjugated per 0.25 to 0.5 mg of polyethylenimine polymer.

18. The method of claim 17 wherein 18.6 to 112 molar equivalents of active moiety is conjugated per 0.5 mg of activated polyethylenimine polymer.

19. The method of claim 18 wherein 112 molar equivalents of active moiety is conjugated per 0.5 mg of activated polyethylenimine polymer.

20. The method of claim 1 wherein the active moiety is streptavidin.

21. The method of claim 1 wherein the active moieties are selected from the group consisting of photoproteins, enzymes and fluorophores.

22. The method of claim 1 wherein the active moiety is an antibody.

23. The method of claim 22 wherein the antibody is comprised of a mixture of a rabbit IgG and a mouse IgG.

24. The method of claim 23 wherein the ratio of rabbit IgG to mouse IgG is between 1-10 and 10-1.

25. The method of claim 1 wherein the active moiety is one or more IgG.

26. The method of claim 1 wherein the active moiety is streptavidin or polystreptavidin.

27. A compound comprising a polyethylenimine polymer conjugated to an active moiety, made by the method of claim 1, wherein such compound is water soluble.

* * * * *